United States Patent
Wei et al.

(10) Patent No.: US 10,307,079 B2
(45) Date of Patent: Jun. 4, 2019

(54) METHOD AND SYSTEM FOR SURGICAL INSTRUMENT GUIDANCE AND TRACKING WITH POSITION AND ORIENTATION CORRECTION

(71) Applicant: EDDA TECHNOLOGY, INC., Princeton, NJ (US)

(72) Inventors: Guo-Qing Wei, Plainsboro, NJ (US); Xin Dou, Princeton, NJ (US); Li Fan, Belle Mead, NJ (US); Xiaolan Zeng, Princeton, NJ (US); Jian-Zhong Qian, Princeton Junction, NJ (US); Cheng-Chung Liang, West Windsor, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 600 days.

(21) Appl. No.: 14/603,959

(22) Filed: Jan. 23, 2015

(65) Prior Publication Data

US 2015/0208948 A1 Jul. 30, 2015

Related U.S. Application Data (60) Provisional application No. 61/931,960, filed on Jan. 27, 2014.

(51) Int. Cl.
*A61B 5/06* (2006.01)
*A61B 6/12* (2006.01)
(Continued)

(52) U.S. Cl.
CPC ............... *A61B 5/066* (2013.01); *A61B 6/12* (2013.01); *A61B 6/463* (2013.01); *A61B 6/50* (2013.01);
(Continued)

(58) Field of Classification Search
CPC ............. G06T 7/75; G06T 2207/10072; G06T 2207/30021; G06T 2207/30096;
(Continued)

(56) References Cited

U.S. PATENT DOCUMENTS 8,527,033 B1 9/2013 Williams et al.
2006/0025677 A1* 2/2006 Verard .................. A61B 90/36
600/423
(Continued)

FOREIGN PATENT DOCUMENTS

EP 2356940 A1 8/2011
WO 9838919 A2 9/1998
WO 2013102827 A1 7/2013

OTHER PUBLICATIONS

International Search Report and Written Opinion dated Apr. 21, 2015 in International Application PCT/US2015/12829.
(Continued)

*Primary Examiner* — Bo Joseph Peng
(74) *Attorney, Agent, or Firm* — Pillsbury Winthrop Shaw Pittman LLP (57) ABSTRACT

The present teaching relates to surgical procedure assistance. In one example, a first image of an organ having a lesion is obtained prior to a surgical procedure. Information related to a pose of a surgical instrument at a first location with respect to the lesion is received from a sensor coupled with the surgical instrument. A visual environment having the lesion and the surgical instrument rendered therein is generated based on the first image and the information received from the sensor. A second image of the organ is obtained when the surgical instrument is moved to a second location with respect to the lesion during the surgical procedure. The second image captures the lesion and the surgical instrument. The pose of the surgical instrument and
(Continued)

the lesion rendered in the visual environment are adjusted based, at least in part, on the second image.

21 Claims, 7 Drawing Sheets

(51) Int. Cl.
*A61B 6/00* (2006.01)
*A61B 34/20* (2016.01)
*G06T 7/73* (2017.01)
*A61B 6/03* (2006.01)

(52) U.S. Cl.
CPC ............ *A61B 6/5235* (2013.01); *A61B 34/20* (2016.02); *G06T 7/75* (2017.01); *A61B 6/032* (2013.01); *A61B 6/527* (2013.01); *A61B 2034/2051* (2016.02); *A61B 2034/2055* (2016.02); *G06T 2207/10072* (2013.01); *G06T 2207/30021* (2013.01); *G06T 2207/30096* (2013.01)

(58) Field of Classification Search
CPC .. A61B 5/066; A61B 6/12; A61B 6/50; A61B 6/5235; A61B 34/20; A61B 6/463; A61B 6/032; A61B 2034/2055; A61B 6/527; A61B 2034/2051
See application file for complete search history.

(56) References Cited

U.S. PATENT DOCUMENTS

| | | |
|---|---|---|
| 2008/0214922 A1 | 9/2008 | Hartmann et al. |
| 2009/0292201 A1 | 11/2009 | Kruecker |
| 2010/0168763 A1 | 7/2010 | Zhao et al. |
| 2010/0268067 A1* | 10/2010 | Razzaque ............ A61B 8/4245 600/424 |
| 2011/0268339 A1 | 11/2011 | Volokh et al. |

OTHER PUBLICATIONS

International Preliminary Report on Patentability dated Aug. 11, 2016 in International Application PCT/US2015/012829.
Extended European Search Report dated Jan. 17, 2018 in European Application 15740624.0.
Office Action dated Oct. 12, 2018 in Chinese Application 201580016937.0.

* cited by examiner

METHOD AND SYSTEM FOR SURGICAL INSTRUMENT GUIDANCE AND TRACKING WITH POSITION AND ORIENTATION CORRECTION

CROSS-REFERENCE TO RELATED APPLICATIONS

The present application claims priority to U.S. Provisional Application Ser. No. 61/931,960, filed Jan. 27, 2014, entitled "Needle Guidance and Tracking in Percutaneous Interventions Through Incremental Reset of Needle and Lesion Positions," which is incorporated herein by reference in its entirety.

BACKGROUND

1. Technical Field

The present teaching relates to surgical procedure assistance. More specifically, the present teaching is directed methods, systems, and programming for surgical instrument guidance and tracking.

2. Discussion of Technical Background

For biopsy of tumors and for minimally invasive treatment of cancers by, e.g. radiofrequency ablation, the placement of needles and ablation probes to the target is one of the steps of the procedures. The current state of the art is to use an imaging device to guide the placement step by step. First, the patient is scanned with a computed tomography (CT) or magnetic resonance imaging (MRI) device. Then one or more needle paths are planned on the acquired images by determining appropriate needle entrance points on the skin and target points for each needle. Then one or more needles are placed into the patient body by moving the needles step by step toward the targets. In each step, only a small movement of the needle is made. This is due to safety reasons and due to the lack of a guidance system. After each step of needle advancement, the patient is scanned again with the imaging devices to check whether the planned path is being followed. Adjustment of the needle orientation is then made if it is found that the actual needle path would not reach the target if the current needle orientation is kept. After the needle orientation is adjusted, the needle is advanced for another step. Then the imaging device is used again to check the needle orientation for another possible adjustment of the needle. This step is repeated until the needle tip reaches the target position.

The above-mentioned image-guided method makes sure that the needle can reach the desired location. However, it is a time-consuming procedure. For lesions located in difficult positions, such as lesions deep in the organ or close to critical organs, such as major vessel branch, heart, or lung lobe fissures, only a small step may be advanced toward the target lesion for a more careful check of the needle position for each needle pass. In such situations, more than the usual number of needle passes may be needed. Ten or more needle passes may be needed. This poses extra radiation dose to the patient if CT imaging device is used. To overcome those problems, image-guided needle tracking systems have been developed, e.g., in U.S. Patent Application Publication No. 2012/0029387, Guo-Qing Wei, Jian-Zhong Qian, Cheng-Chung Liang, Xiaolan Zeng, Li Fan, Feng Ma, "Methods and systems for real-time surgical procedure assistance using an electronic organ map". In such a system, an electromagnetic sensor is attached to the needle. After appropriate calibration and registration, the needle position and orientation is displayed in real-time in the CT image space and overlaid onto the CT images. The aiming of the needle to the target and advancement of the needle may be monitored in real-time, and it may be immediately seen whether the needle is in the right direction and whether it may hit the target before the needle is advanced. This technology reduces the number of passes to reach a target. Instead of trial-and-error, such a system also gives physicians greater confidence in performing the procedure.

Even with real-time needle tracking, more than one needle passes may still be needed to reach the target, especially for lesions in critical locations. Due to possible lesion position shift caused by breathing or tissue damage from needle, re-adjustment of the needle position and orientation may still be needed. The images acquired for each needle adjustment are currently not utilized by the tracking system to further improve the accuracy of the guidance for the next step of needle advancement. It is then highly desirable to utilize the information in the new images to update the tracking system, so that a more accurate guidance may be performed.

SUMMARY

The present teaching relates to surgical procedure assistance. More specifically, the present teaching is directed methods, systems, and programming for surgical instrument guidance and tracking.

In one example, a method implemented on a computing device having at least one processor, storage, and a communication platform connected to a network for surgical procedure assistance is disclosed. A first image of an organ having a lesion is obtained prior to a surgical procedure. Information related to a pose of a surgical instrument at a first location with respect to the lesion is received from a sensor coupled with the surgical instrument. A visual environment having the lesion and the surgical instrument rendered therein is generated based on the first image and the information received from the sensor. A second image of the organ is obtained when the surgical instrument is moved to a second location with respect to the lesion during the surgical procedure. The second image captures the lesion and the surgical instrument. The pose of the surgical instrument and the lesion rendered in the visual environment are adjusted based, at least in part, on the second image.

In another example, a method implemented on a computing device having at least one processor, storage, and a communication platform connected to a network for instrument tracking and guidance is disclosed. A first image of an object is obtained prior to an operation. Information related to a pose of an instrument at a first location with respect to the object is received from a sensor coupled with the instrument. A visual environment having the object and the instrument rendered therein is generated based on the first image and the information received from the sensor. A second image capturing the object and the instrument is obtained when the instrument is moved to a second location with respect to the object during the operation. The pose of the instrument and the object rendered in the visual environment are adjusted based, at least in part, on the second image.

In a different example, a system for surgical procedure assistance is disclosed. The system includes a tracking unit, a positioning unit, and one or more compensation units. The tracking unit is configured to receive information related to a pose of a surgical instrument at a first location with respect to a lesion from a sensor coupled with the surgical instrument. The positioning unit is configured to obtain a first image of an organ having the lesion prior to a surgical procedure and generate a visual environment having the lesion and the surgical instrument rendered therein based on the first image and the information received from the sensor. The positioning unit is further configured to obtain a second image of the organ when the surgical instrument is moved to a second location with respect to the lesion during the surgical procedure, wherein the second image captures the lesion and the surgical instrument. The one or more compensation units are configured to adjust the pose of the surgical instrument and the lesion rendered in the visual environment based, at least in part, on the second image.

Other concepts relate to software for implementing the present teaching on surgical instrument guidance and tracking. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure assistance is disclosed. The recorded information, when read by the machine, causes the machine to perform a series of processes. A first image of an organ having a lesion is obtained prior to a surgical procedure. Information related to a pose of a surgical instrument at a first location with respect to the lesion is received from a sensor coupled with the surgical instrument. A visual environment having the lesion and the surgical instrument rendered therein is generated based on the first image and the information received from the sensor. A second image of the organ is obtained when the surgical instrument is moved to a second location with respect to the lesion during the surgical procedure. The second image captures the lesion and the surgical instrument. The pose of the surgical instrument and the lesion rendered in the visual environment are adjusted based, at least in part, on the second image.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

The present teaching relates to an interactive 3D guidance system for soft organ operation based on incremental reset of surgical instruments, e.g., needles, and lesion position in interventional procedures. The system can be realized as a specialized and networked system by utilizing one or more computing devices (e.g., mobile phone, personal computer, etc.) and network communications (wired or wireless).

Figure 1:
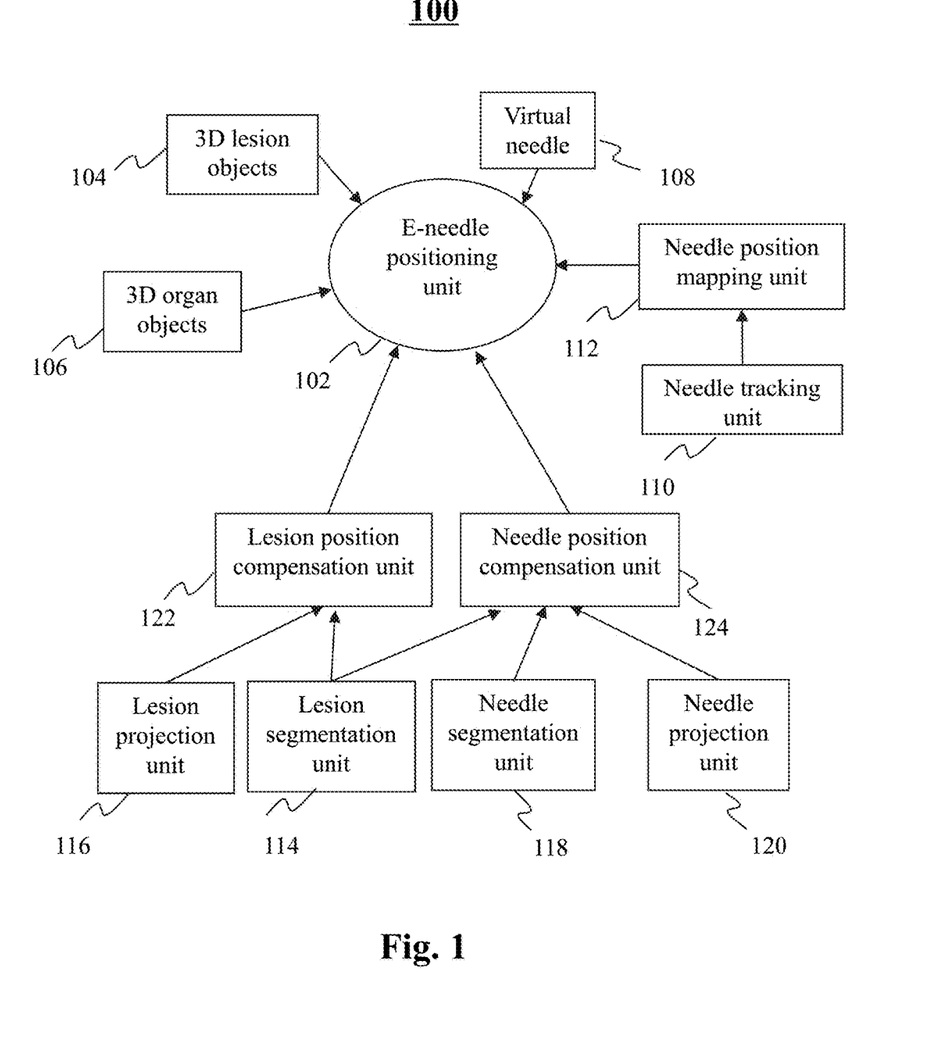
FIG. 1 shows an exemplary system diagram for a needle guidance system in terms of incremental lesion and needle reset and real-time tracking, according to one embodiment of the present teaching.

FIG. 1 shows an exemplary system diagram of a system 100 for facilitating needle guidance based on utilization of newly acquired images for incremental reset of lesion position and incremental reset of a virtual needle's pose (position and orientation) for tracking, according to an embodiment of the present teaching. It is understood that although "needle" is discussed in the present teaching, the guidance and tracking system and method disclosed in the present teaching can be applied to any other suitable instrument used in biopsy and interventional procedures, such as but not limited to probes, knifes, catheters, etc. The system 100 includes an electronic-needle (e-needle) positioning unit 102, a needle tracking unit 110, a needle position mapping unit 112, a lesion segmentation unit 114, a lesion projection unit 116, a needle segmentation unit 118, a needle projection unit 120, a lesion position compensation unit 122, and a needle position compensation unit 124.

First, a preoperative scan of a patient may be acquired right before the procedure. The scan may be a CT, a MRI, or any other image modalities. The images are referred as "preoperative images" in the present teaching. From the preoperative images, the target lesions may be segmented and displayed as 3D lesion objects 104 by the e-needle positioning unit 102. The e-needle positioning unit 102 may produce a 3D visualization environment, in which all objects may be displayed in 3D. The e-needle positioning unit 102 may also display 2D images with interested objects overlaid. Interested organs, such as but not limited to, liver, lung, kidney, and vascular structures, may be also segmented and displayed as 3D organ objects 106 by the e-needle positioning unit 102. A physical needle may also be simulated by the e-needle positioning unit 102 and displayed as a virtual needle 108. More than one needle may be simulated. The e-needle positioning unit 102 is also referred as "the navigation space" in the present teaching.

The needle tracking unit 110 in this embodiment tracks the needle's pose (position and orientation) through either magnetic sensors or optical sensors that are attached to the needle, or any other suitable tracking mechanisms. Through the needle position mapping unit 112, the needle position and orientation in the sensor space is mapped into the coordinate space of the e-needle positioning unit 102, i.e. the navigation space. The coordinate space of the e-needle positioning unit 102 may be the same as the coordinate space of the preoperative images. The mapping may be pre-computed using the known methods, such as the method disclosed in U.S. Patent Application Publication No. 2012/0029387, Guo-Qing Wei, Jian-Zhong Qian, Cheng-Chung Liang, Xiaolan Zeng, Li Fan, Feng Ma, "Methods and systems for real-time surgical procedure assistance using an electronic organ map," which is incorporated by reference in its entirety. The mapped needle position and orientation may be used to visualize the virtual needle's position and orientation in real-time, so that when the physical needle moves, the virtual needle moves simultaneously.

By positioning and orientating the physical needle so that the virtual needle is aimed at the target 3D lesion objects 104 in the e-needle positioning unit 102, the physical needle is believed to have aimed at the true lesion in the patient body. When this aiming is achieved, the needle is inserted into the patient body for a certain length. With the needle in the body, a new scan of the patient may be made. This scan is usually covering only part of the body, namely a section where the lesion and needle are located. In the present teaching, such a scan is referred as "sectional scan," or "sectional CT" for CT imaging device. From the sectional scan images, the lesion may be segmented through the lesion segmentation unit 114, and the needle may be segmented through the needle segmentation unit 118. The segmentations may be performed either automatically or manually. The lesion in the preoperative images may be mapped to the sectional scan space through the lesion projection unit 116 to obtain a predicted lesion. The mapping may be achieved through known image registration techniques by registering the preoperative images with sectional scan images. The positional difference between the segmented lesion and the predicted lesion may then be computed by the lesion position compensation unit 122 to adjust the lesion position in the system 100. The positional change of lesion may be caused by either breathing or tissue damage by needle, thus causing the lesion to shift. In another embodiment of the present teaching, the lesion may not be segmented. The lesion position compensation unit 122 may take human input, e.g., mouse-dragging of the mapped lesion onto the actual lesion position, to compute the lesion position compensation amount. This lesion position compensation is used to reflect the latest lesion position as found in the sectional scan into the e-needle positioning unit 102.

From the sectional scan images, the needle may be segmented, either automatically or manually, by the needle segmentation unit 118. Manual segmentation may be performed, for example, by mouse-clicking on the needle tip or any point of the needle. The needle projection unit 120 may project the virtual needle onto the sectional scan images based on the geometrical transformation from the preoperative image space onto the sectional image space. The difference in position and orientation between the segmented needle and projected needle may be used to reset the virtual needle position by the needle position compensation unit 124. The needle position may be updated by changing the ending position of the needle, whereas the needle orientation may be reset by rotating the virtual needle so that the projected needle aligns with the segmented one. The new position and orientation of the virtual needle represents the needle position that is consistent with the needle position in the sectional scan. It will also be the starting position for needle tracking in the next step for needle guidance. After both the lesion position and needle position are adjusted in the e-needle positioning unit 102, the 3D visualization may be based on the new positions for needle tracking.

Figure 2:
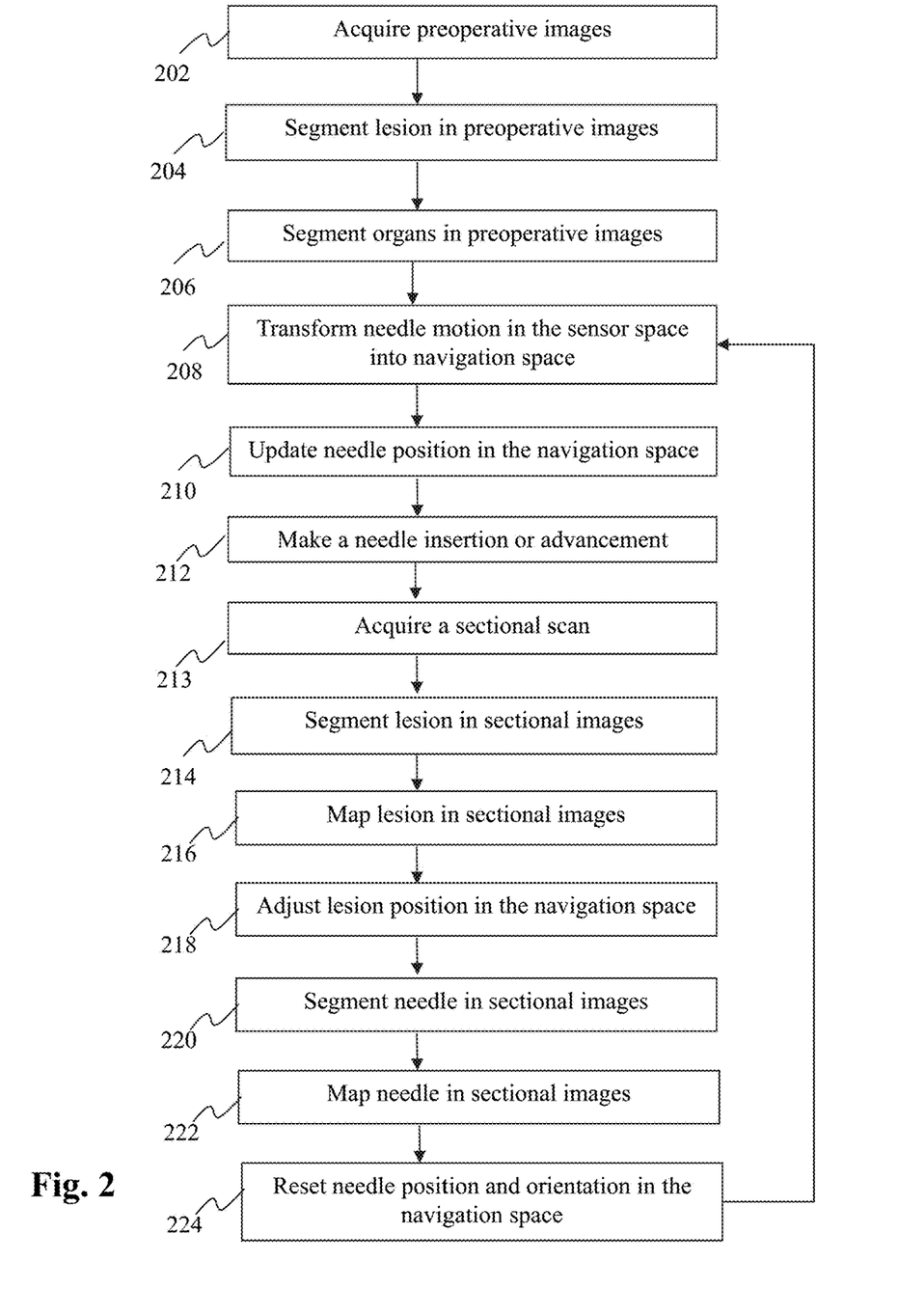
FIG. 2 shows an exemplary flow diagram according to one embodiment of the present teaching for needle guidance and tracking which uses sectional scans to reset lesion position and needle position and orientation.

FIG. 2 illustrates an exemplary workflow of the system 100, according to one embodiment of the present teaching. At 202, a preoperative image of a patient may be acquired. At 204, the target lesion may be segmented. More than one lesion may be segmented. Other anatomical structures, such as liver, lung, kidney or vascular structures, may also be segmented at 206. The target lesion and the segmented organs may be visualized in the navigation space, so that spatial relationships between the lesion and the anatomical structures may be examined. As another embodiment of the present teaching, the interested anatomical structures may be segmented in a scan acquired in an earlier date for diagnosis purposes in the same or different imaging modality as the preoperative scan. This scan may be referred as "the diagnostic scan" in the present teaching. The segmented anatomical structure may be mapped into the preoperative scan image space through an image registration between the diagnostic scan and the preoperative scan. At 208, needle motion in the sensor space may be transformed into the motion in the navigation space. This motion is used to update the virtual needle's position and orientation in the navigation space at 210. Based on the display of the needle, the target lesion, and other organs, user may make a needle insertion, or adjust the needle orientation to aim at the target lesion at 212. The distance to move the needle forward is up to user's decision. At 213, a sectional scan of the patient may be made to confirm the needle position. From the sectional scan images, the target lesion may be segmented at 214. The lesion segmented in the preoperative images may be mapped to the sectional scan image space at 216. The mapping may be performed by any suitable image registration techniques that register preoperative images with sectional images. From the mapping, a mapped lesion may be obtained. The mapped lesion may be overlaid onto the sectional images, so that its spatial relationship to the segmented lesion in the sectional images may be visually examined. The positional difference between the segmented lesion and mapped lesion may reflect lesion positional shift caused by breathing or tissue damage. At 218, this positional difference of lesion may be used to adjust the lesion position in the navigation space.

From the sectional images, the needle may also be segmented at 220. In case of lesion ablation, more than one needle may be segmented. The needle in the navigation space may be mapped into the sectional image space at 222. The position and orientation difference between the segmented needle and the mapped needle may be used to reset the needle position and orientation for the virtual needle in the navigation space at 224. The adjusted needle position may be used for needle tracking in the next needle advancement. The steps from 208 to 224 may repeat until the target lesion is reached.

Figure 3:
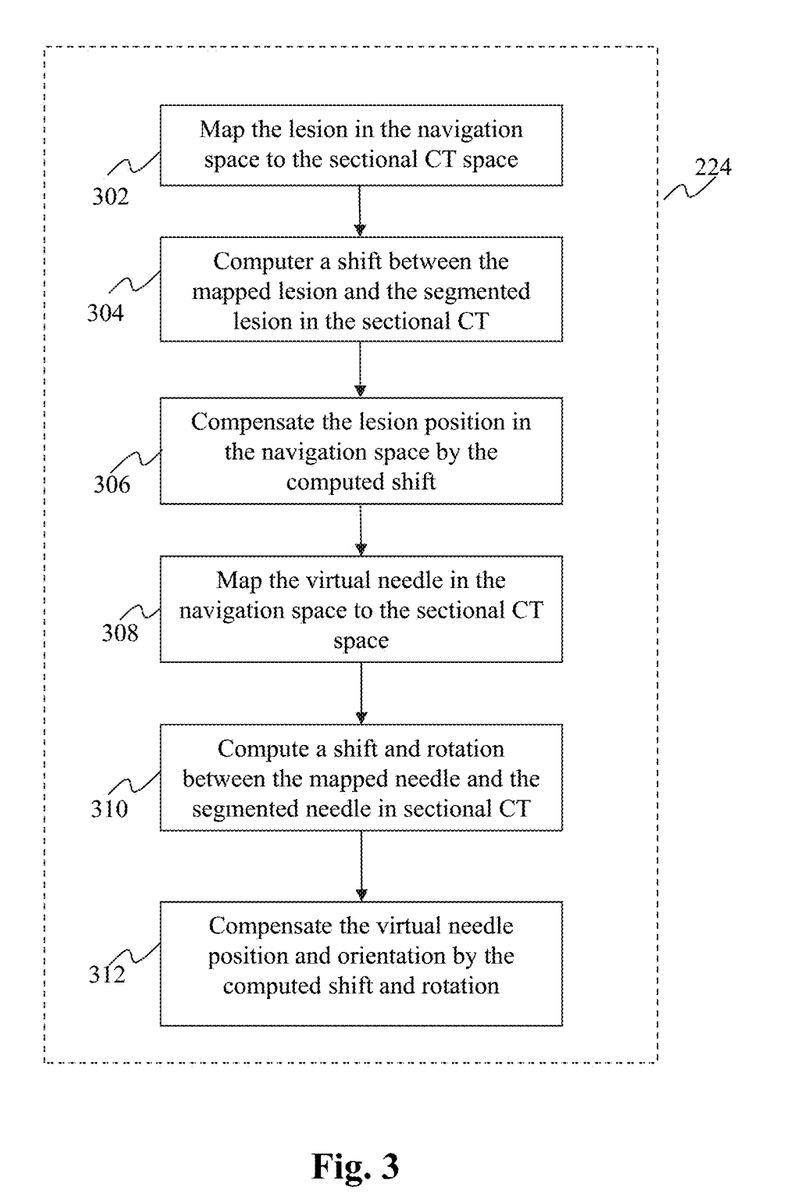
FIG. 3 shows an exemplary flow diagram according to one embodiment of the present teaching for needle position and orientation reset.

An exemplary workflow of the needle position updating at 224 is shown in FIG. 3. At 302, the lesion in the navigation space is mapped to the sectional image space. A shift between the centers of the mapped lesion and the segmented lesion may be computed at 304. At 306 the lesion position in the navigation space is updated by the computed shift. At 308, the virtual needle in the navigation space is mapped to the sectional image space. At 310, a shift and a rotation between the virtual needle and the segmented needle may be computed. This shift and rotation may be used to compensate the position and orientation of the virtual needle at 312.

Figure 4:
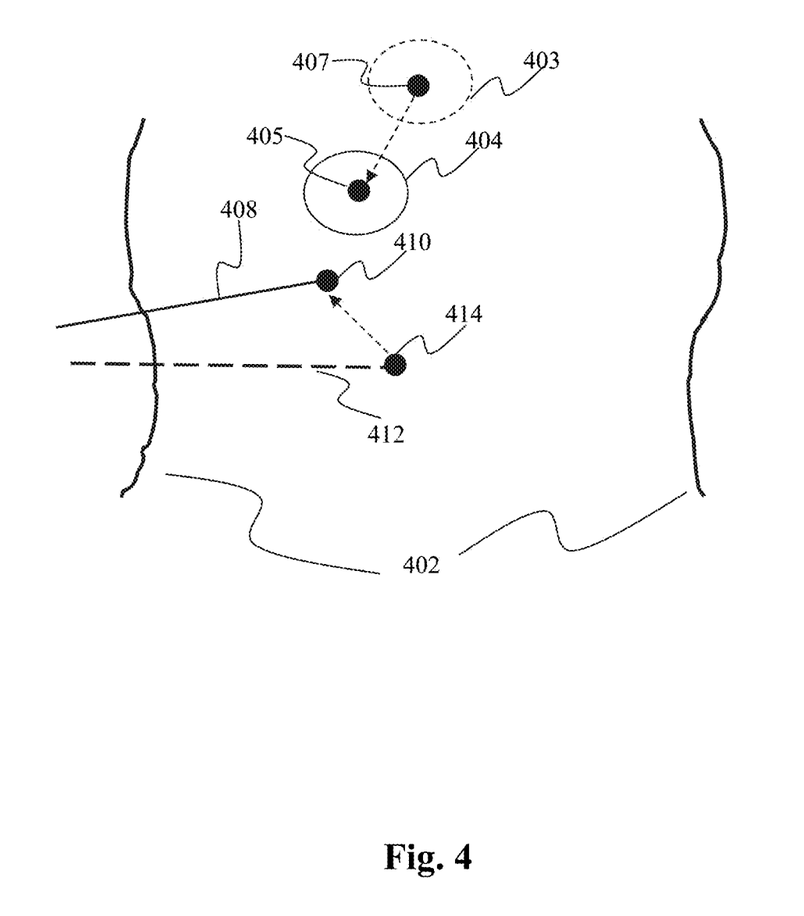
FIG. 4 illustrates the spatial relationship between patient body, segmented lesion, mapped lesion, segmented needle and mapped needle in the sectional CT space, according to one embodiment of the present teaching.

FIG. 4 is an exemplary illustration of the lesion and needle position compensation method. In FIG. 4, 402 is the segmented organ, 404 is the segmented lesion, 405 is the center of the segmented lesion. 403 is the mapped lesion, whereas 407 is the center of the mapped lesion. The shift between 407 and 405 is used to reset the lesion position in the navigation space. 408 is the segmented needle, whereas 410 is the tip of the segmented needle. 412 is the mapped needle, whereas 414 is the tip of the mapped needle. A shift between the segmented needle tip and the mapped needle tip may be represented by the arrow from 414 and 410, whereas a rotation may be represented by rotating the mapped needle by the angle between the segmented needle 408 and the mapped needle 412. By the operations above the relative position and orientation between the needle and lesion in the navigation space may be made the same as that in the sectional image space.

Figure 5:
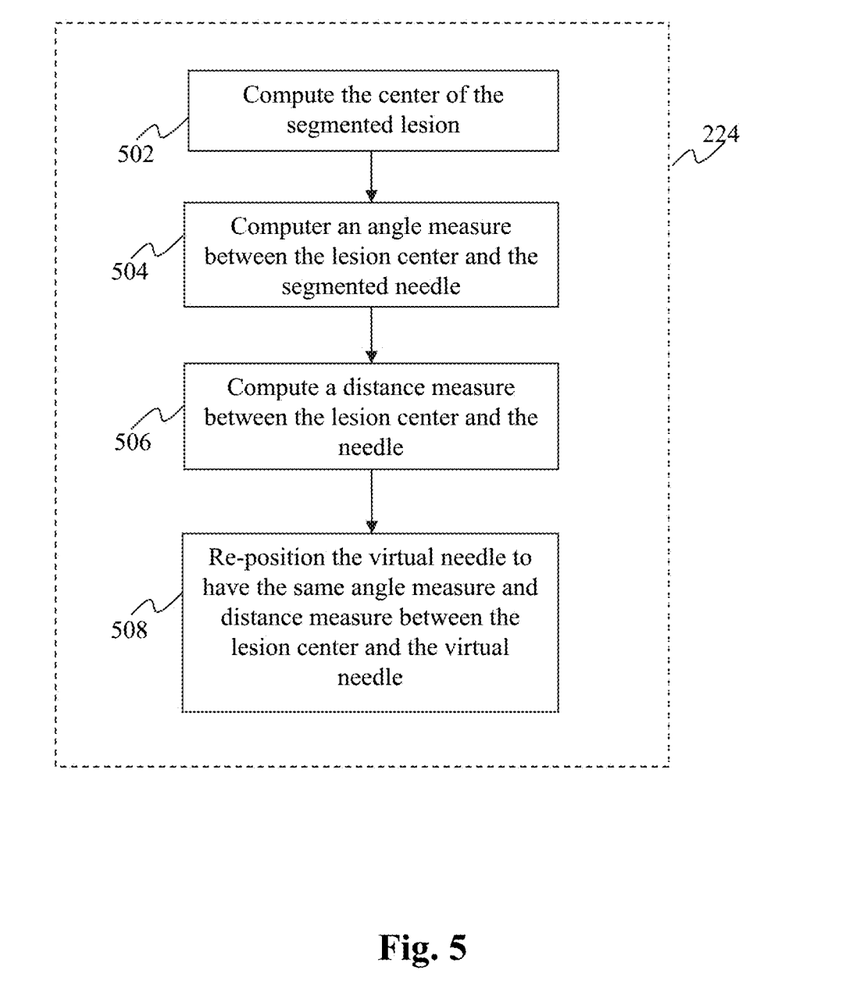
FIG. 5 shows another exemplary flow diagram according to one embodiment of the present teaching for needle position and orientation reset.

Another exemplary workflow of the needle position updating 224 is shown in FIG. 5. At 502, the center of the segmented lesion may be computed. At 504, an angle measurement between the lesion and the segmented needle may be computed as the angle between the needle and the line joining the lesion center and the needle entrance point on the skin. At 506, a distance measure is obtained as the difference between the needle length within the body and the distance from the lesion center to the skin entrance point of the needle. At 508, the virtual needle may be repositioned to have the same angle measure and distance measure.

Figure 6:
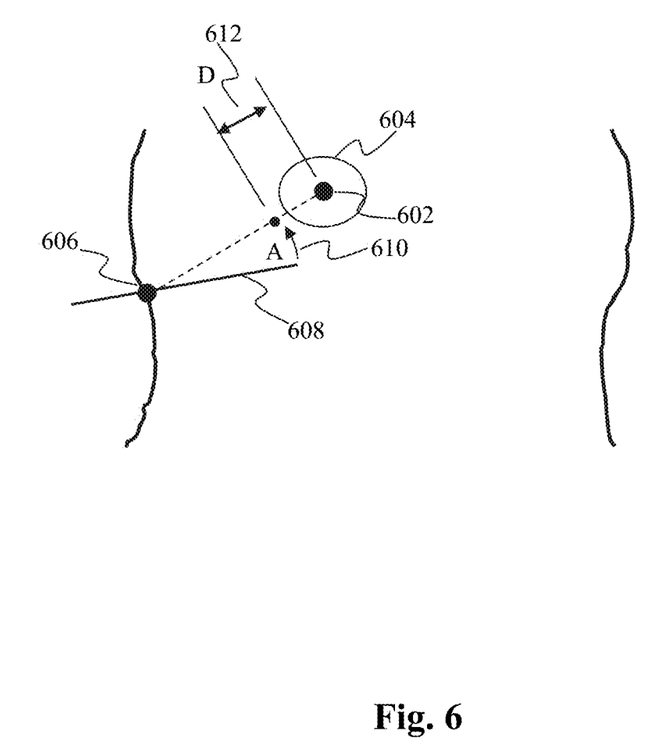
FIG. 6 illustrates how the angular measure and distance measure between the lesion and needle may be computed for needle position and orientation reset according to one embodiment of the present teaching.

FIG. 6 illustrates the computation of the angle measure and the distance measure described in FIG. 5. 604 is the lesion, 602 is the center of the lesion, 608 is the segmented needle, 606 is the skin entrance point of the needle. 610 is the angle, dented by A, between the needle 608 and the line joining the lesion center and the skin entrance point of the needle. Suppose L is the distance between the lesion center and the skin entrance point, N is the needle length within body, namely the distance between the tip of the needle and the skin entrance point. Then distance measure D, denoted as 612, may be computed as $D=L-N$.

The angle measure A and distance measure D reflects the relative position between the lesion and the needle. These two measures uniquely define how the needle may move to reach the target: rotate the needle by angle A, followed by forward movement of distance D. In the navigation space, the virtual needle may be re-positioned so as to have the same angular measure A and same distance measure D with respect to the lesion. The lesion may remain the same position. After the needle is reset to this new position and orientation, the needle movement in the navigation space will start to follow movement of sensors on the physical needle.

To implement various modules, units, and their functionalities described in the present disclosure, computer hardware platforms may be used as the hardware platform(s) for one or more of the elements described herein (e.g., the system 100 described with respect to FIGS. 1-6). The hardware elements, operating systems and programming languages of such computers are conventional in nature, and it is presumed that those skilled in the art are adequately familiar therewith to adapt those technologies to needle guidance as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 7:
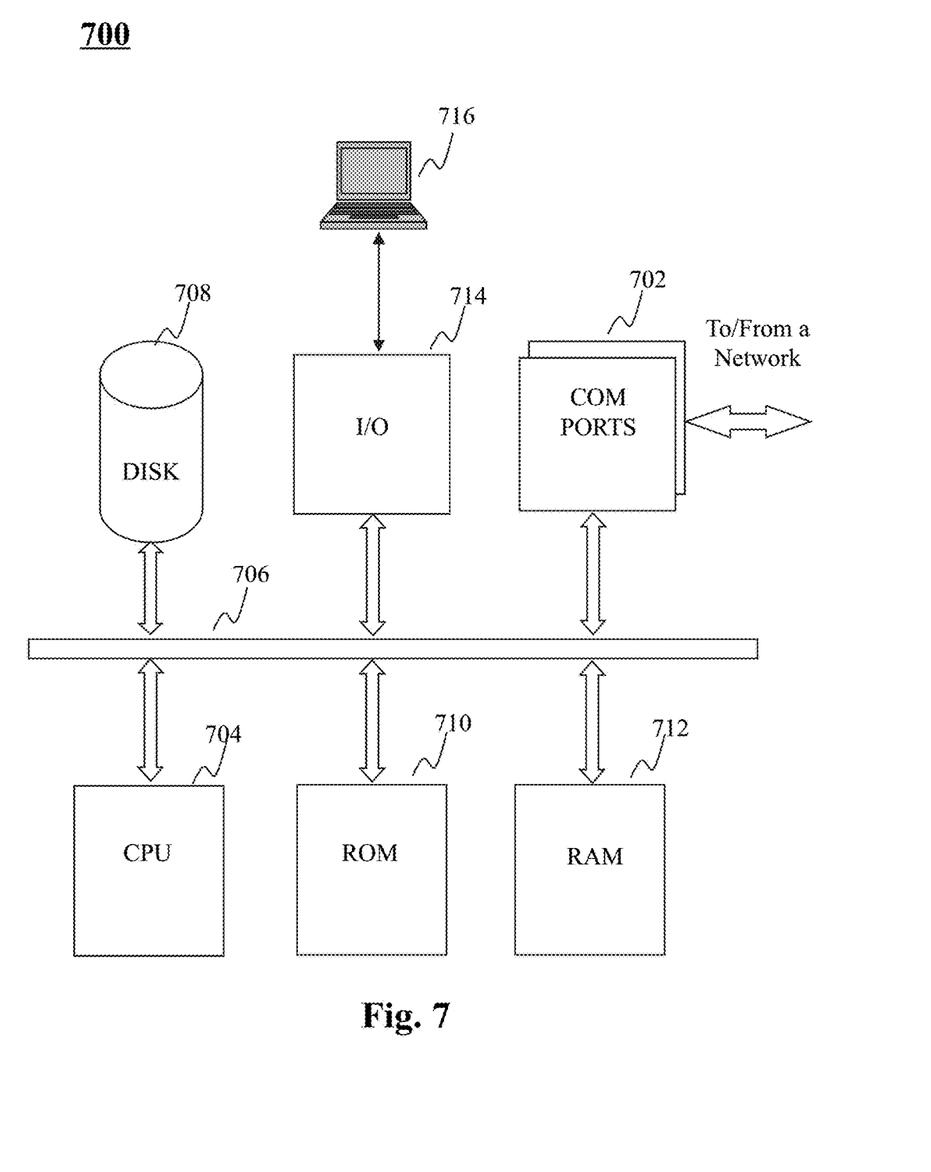
FIG. 7 depicts the architecture of a computer which can be used to implement a specialized system incorporating the present teaching

FIG. 7 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 700 may be used to implement any component of needle guidance techniques, as described herein. For example, the system 100 may be implemented on a computer such as computer 700, via its hardware, software program, firmware, or a combination thereof. Although only one such computer is shown, for convenience, the computer functions relating to needle guidance as described herein may be implemented in a distributed fashion on a number of similar platforms, to distribute the processing load.

The computer 700, for example, includes COM ports 702 connected to and from a network connected thereto to facilitate data communications. The computer 700 also includes a central processing unit (CPU) 704, in the form of one or more processors, for executing program instructions. The exemplary computer platform includes an internal communication bus 706, program storage and data storage of different forms, e.g., disk 708, read only memory (ROM) 710, or random access memory (RAM) 712, for various data files to be processed and/or communicated by the computer, as well as possibly program instructions to be executed by the CPU 704. The computer 700 also includes an I/O component 714, supporting input/output flows between the computer and other components therein such as user interface elements 716. The computer 700 may also receive programming and data via network communications.

Hence, aspects of the methods of needle guidance and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a search engine operator into the hardware platform(s) of a computing environment or other system implementing a computing environment or similar functionalities in connection with user interest inference. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the needle guidance system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, comprising:
   obtaining a first image of an organ having a lesion prior to a surgical procedure;
   receiving information, related to a pose of a surgical instrument at a first location with respect to the lesion, from a sensor coupled with the surgical instrument;
   generating a visual environment having the lesion and the surgical instrument rendered therein based on the first image and the information received from the sensor;
   obtaining a second image of the organ when the surgical instrument is disposed at a second location with respect to the lesion during the surgical procedure, wherein the second image captures the lesion and the surgical instrument;
   mapping the lesion in the first image to the second image;
   mapping the surgical instrument rendered in the visual environment to the second image; and
   adjusting the pose of the surgical instrument and the lesion rendered in the visual environment, wherein the adjusting comprises compensating a difference in pose of the surgical instrument in the visual environment and in the second image, and compensating a position difference of the lesion in the first and second images.

2. The method of claim 1, wherein the pose of the surgical instrument rendered in the visual environment is adjusted by compensating a position difference and/or an orientation difference of the surgical instrument in the visual environment and in the second image.

3. The method of claim 2, wherein compensating the position difference and/or the orientation difference of the surgical instrument comprises:
   computing a distance between a tip of the mapped surgical instrument and a tip of the surgical instrument in the second image; and
   computing an angle between a direction of the mapped surgical instrument and a direction of the surgical instrument in the second image.

4. The method of claim 1, wherein the pose of the surgical instrument rendered in the visual environment is adjusted based on a distance measure and an angle measure between the lesion and the surgical instrument in the second image.

5. The method of claim 4, wherein the distance measure and the angle measure are computed based on the center of the lesion in the second image, a point in the second image at which the at least one surgical instrument enters a patient's body, and a tip of the at least one surgical instrument in the second image.

6. The method of claim 1, wherein compensating the position difference of the lesion comprises:
   computing a distance between the center of the mapped lesion from the first image and the center of the lesion in the second image.

7. The method of claim 1, wherein the surgical instrument includes a needle.

8. The method of claim 1, wherein the steps of receiving, generating, obtaining, and adjusting are repeated until the surgical instrument reaches the lesion during the surgical procedure.

9. A system for surgical procedure assistance, comprising:
   a tracking unit implemented by a processor and configured to receive information related to a pose of a surgical instrument at a first location with respect to a lesion from a sensor coupled with the surgical instrument;
   a positioning unit implemented by a processor and configured to:
      obtain a first image of an organ having the lesion prior to a surgical procedure,
      generate a visual environment having the lesion and the surgical instrument rendered therein based on the first image and the information received from the sensor, and obtain a second image of the organ when the surgical instrument is disposed at a second location with respect to the lesion during the surgical procedure, wherein the second image captures the lesion and the surgical instrument; and a compensation unit implemented by the processor and configured to:

map the lesion in the first image to the second image, map the surgical instrument rendered in the visual environment to the second image, and adjust the pose of the surgical instrument and the lesion rendered in the visual environment by compensating a difference in pose of the surgical instrument in the visual environment and in the second image, and compensating a position difference of the lesion in the first and second images.

10. The system of claim 9, wherein the one or more compensation units comprise a second compensation unit configured to compensate a position difference and/or an orientation difference of the surgical instrument in the visual environment and in the second image.

11. The system of claim 10, wherein the second compensation unit is further configured to:

compute a distance between a tip of the mapped surgical instrument and a tip of the surgical instrument in the second image; and compute an angle between a direction of the mapped surgical instrument and a direction of the surgical instrument in the second image.

12. The system of claim 9, wherein the pose of the surgical instrument rendered in the visual environment is adjusted based on a distance measure and an angle measure between the lesion and the surgical instrument in the second image.

13. The system of claim 12, wherein the distance measure and the angle measure are computed based on the center of the lesion in the second image, a point in the second image at which the at least one surgical instrument enters a patient's body, and a tip of the at least one surgical instrument in the second image.

14. The system of claim 9, wherein the first compensation unit is further configured to:

compute a distance between the center of the mapped lesion from the first image and the center of the lesion in the second image.

15. The system of claim 9, wherein the surgical instrument includes a needle.

16. A non-transitory machine readable medium having information recorded thereon for surgical procedure assistance, wherein the information, when read by a machine, causes the machine to perform the steps of:

obtaining a first image of an organ having a lesion prior to a surgical procedure;

receiving information, related to a pose of a surgical instrument at a first location with respect to the lesion, from a sensor coupled with the surgical instrument;

generating a visual environment having the lesion and the surgical instrument rendered therein based on the first image and the information received from the sensor;

obtaining a second image of the organ when the surgical instrument is disposed at a second location with respect to the lesion during the surgical procedure, wherein the second image captures the lesion and the surgical instrument;

mapping the lesion in the first image to the second image;

mapping the surgical instrument rendered in the visual environment to the second image; and adjusting the pose of the surgical instrument and the lesion rendered in the visual environment, wherein the adjusting comprises compensating a difference in pose of the surgical instrument in the visual environment and in the second image, and compensating a position difference of the lesion in the first and second images.

17. The medium of claim 16, wherein the pose of the surgical instrument rendered in the visual environment is adjusted by compensating a position difference and/or an orientation difference of the surgical instrument in the visual environment and in the second image.

18. The medium of claim 16, wherein the pose of the surgical instrument rendered in the visual environment is adjusted based on a distance measure and an angle measure between the lesion and the surgical instrument in the second image.

19. The medium of claim 16, wherein the steps of receiving, generating, obtaining, and adjusting are repeated until the surgical instrument reaches the lesion during the surgical procedure.

20. A method, implemented on a computing device having at least one processor, storage, and a communication platform capable of connecting to a network for instrument tracking and guidance, comprising:

obtaining a first image of an object prior to an operation;

receiving information, related to a pose of an instrument at a first location with respect to the object, from a sensor coupled with the instrument;

generating a visual environment having the object and the instrument rendered therein based on the first image and the information received from the sensor;

obtaining a second image capturing the object and the instrument when the instrument is disposed at a second location with respect to the object during the operation; and adjusting the pose of the instrument and the object rendered in the visual environment based on mapping of the object in the first image to the second image, and mapping of the instrument rendered in the visual environment to the second image, the adjusting being performed by compensating a difference in pose of the instrument in the visual environment and in the second image, and compensating a position difference of the lesion in the first and second images.

21. The method of claim 20, wherein the object is an organ including a lesion, and the instrument is one of a needle, a catheter, a probe, and a knife.

* * * * *